United States Patent [19]

Krespan

[11] Patent Number: 4,531,011

[45] Date of Patent: Jul. 23, 1985

[54] ALKYL PERFLUORO-OMEGA-(2-IODOETHOXY) COMPOUNDS AND VINYL ETHERS THEREFROM

[75] Inventor: Carl G. Krespan, Wilmington, Del.

[73] Assignee: E. I. Du Pont de Nemours and Company, Wilmington, Del.

[21] Appl. No.: 472,101

[22] Filed: Mar. 4, 1983

[51] Int. Cl.$^3$ .............................................. C07C 69/67
[52] U.S. Cl. ..................................................... 560/184
[58] Field of Search ............................................ 560/184

[56] References Cited

U.S. PATENT DOCUMENTS

| | | | |
|---|---|---|---|
| 3,311,658 | 3/1967 | Warnell | 260/544 |
| 3,351,619 | 3/1967 | Warnell | 260/544 |
| 3,542,859 | 11/1970 | Litt et al. | 562/504 |
| 4,032,566 | 6/1977 | Psarras et al. | 560/184 |
| 4,153,804 | 5/1979 | Yamabe et al. | 560/183 |
| 4,243,770 | 1/1981 | Tatemoto et al. | 525/331 |
| 4,251,399 | 2/1981 | Tomoda et al. | 260/4 R |
| 4,275,226 | 6/1981 | Yamabe et al. | 560/183 |
| 4,335,255 | 6/1982 | Krespan | 560/184 |
| 4,340,750 | 7/1982 | Yamabe et al. | 560/183 |
| 4,357,282 | 11/1982 | Anderson et al. | 260/544 F |
| 4,390,720 | 6/1983 | Resnick | 560/184 |

FOREIGN PATENT DOCUMENTS

| | | |
|---|---|---|
| 125986 | 11/1978 | Japan . |
| 95924 | 8/1981 | Japan . |
| 95925 | 8/1981 | Japan . |
| 2056445 | 3/1981 | United Kingdom . |

OTHER PUBLICATIONS

Derwent Abstract 56022 D/31 (J56 072,002).
Derwent Abstract 68654 D/38 (J56 095,928).
Derwent Abstract 92246 A/51 (J53 131,292).
du Pont de Nemours, *Chemical Abstracts* vol. 96 (1982) #142,282z.
Evans et al., J. Org. Chem. 33 (5), 1839 (1968).

*Primary Examiner*—Natalie Trousof
*Assistant Examiner*—L. Hendriksen
*Attorney, Agent, or Firm*—James A. Costello

[57] ABSTRACT

Alkyl perfluoro-ω-(2-iodoethoxy) compounds, vinyl ethers made therefrom, and a process for preparing the iodo-compounds. The vinyl ether monomers when copolymerized with halogenated 1-olefins are useful to form elastomers, rigid articles, or membranes and films having ion-exchange properties.

6 Claims, No Drawings

ALKYL PERFLUORO-OMEGA-(2-IODOETHOXY) COMPOUNDS AND VINYL ETHERS THEREFROM

BACKGROUND OF THE INVENTION

This invention concerns certain polyfluoro-iodoethoxy compounds, a process therefor, and monomer derivatives thereof. The following publications are representative of the state of the art on polyfluoro-iodoethoxy compounds.

U.S. Pat. Nos. 4,275,226 and 4,340,750 disclose the reaction, $XR_FCOF + C_2F_4 + MF + I_2 \rightarrow XR_FCF_2OCF_2CF_2I$, where X is H, Cl, Br, F, $CO_2R$, —COF, $SO_2F$, CONRR' or $P(O)(OR)_2$; $R_F$ is $C_1$ to $20$ difunctional perfluoro-containing group which can have one or more ether bonds; R is $C_1$ to $10$ alkyl, R' is H or $C_1$ to $10$ alkyl; M is K, Rb or Cs. The compounds $CH_3O_2C(CF_2)_nCF_2OCF_2CF_2I$, where n is 1, 2 or 4 are disclosed but not how to make them. Vinyl ethers devoid of iodine are prepared from the iodo compounds by heating in a solvent in the presence of selected metals: $XR_FCF_2OCF_2CF_2I \rightarrow XR_FCF_2OCF=CF_2$.

U.S. Pat. No. 3,311,658 discloses the compound, $FOCCF(CF_3)[OCF_2CF(CF_3)]_mO(CF_2)_{n+1}I$, and its pyrolysis to the vinyl ether, $CF_2=CF[OCF_2CF(CF_3)]_mO(CF_2)_{n+1}I$, where m is 0 to 5 and n is 1 to 8, preferably 1 or 3. The ω-iodoacyl fluoride is prepared by reacting the compounds $FOC(CF_2)_nI$ with hexafluoropropene oxide (HFPO).

GB No. 2,056,445A discloses preparation of an ω-(2-iodoethoxy)acyl fluoride, $FOC(CF_2)_nOCF_2CF_2I$, where n is 1 to 8, by reacting a perfluorinated lactone and/or a perfluorodiacyl fluoride with tetrafluoroethylene, an iodine source such as $I_2$ or ICl, and fluoride ion in an aprotic solvent. The lactone can be prepared from the compound, $FOC(CF_2)_{2-4}I$.

Evans et al., J. Org. Chem. 33 (5), 1839 (1968) disclose that $I_2$ or ICl can be used in the reaction of perfluorinated ketones with fluoroolefins in the presence of fluoride ions to form ω-(2-iodoethoxy) compounds. However, when the fluoroolefin is tetrafluoroethylene, details are limited to: $XCF_2C(O)CF_3 + KF + C_2F_4 + I_2 \rightarrow XCF_2CF(CF_3)OCF_2CF_2I$ wherein X is F or Cl.

U.S. Pat. No. 4,335,255 discloses fluorinated ketoesters of the formula, $RO_2CCF(CF_3)OCF_2C(O)CF_3$, and HFPO adducts thereof, $RO_2CCF(CF_3)OCF_2CF(CF_3)O[CF(CF_3)CF_2O]_nCF(CF_3)COF$, wherein n is 0 to 6.

U.S. Pat. No. 4,390,720 discloses alkyl-ω-fluoroformyl esters of the formula, $RO_2C—CF(CF_3)O[CF(CF_3)CF_2O]_nCF(CF_3)COF$, wherein n is 0 to 3.

U.S. Pat. No. 4,153,804 discloses ω-fluoroformyl esters of the formula, $RO_2C(R_F)_m[CF_2OCF(CF_3)]_nCOF$, wherein $R_F$ is $C_1$ to $10$ bifunctional perfluoro group, m is 0 or 1, n is 1 to 5 and R is alkyl, prepared by reacting acyl fluorides of the formula, $RO_2C(R_F)_mCOF$, with HFPO.

U.S. Pat. No. 4,032,566 discloses the reaction, $CH_3O_2C—R_F—CF(CF_3)COF + C_2F_4 + KF + ICl \rightarrow CH_3O_2C—R_FCF(CF_3)CF_2OCF_2CF_2I$, wherein $R_F$ is —$(CF_2)_4O[CF(CF_3)CF_2O]_n$ or —$CF(CF_3)OCF_2CF_2O$—, and n is 0 to 10. Also disclosed is a similar reaction employing a diacyl fluoride in place of an ester-acyl fluoride: $FOCCF(CF_3)OCF_2CF_2OCF(CF_3)COF + C_2F_4 + KF + ICl \rightarrow FOCCF(CF_3)OCF_2CF_2OCF(CF_3)CF_2OCF_2CF_2I$. Reaction of this acyl fluoride product with methanol to form the corresponding ester is described.

U.S. Pat. No. 3,351,619 discloses copolymerization of certain vinyl ethers disclosed in U.S. Pat. No. 3,311,658 with halogenated α-olefins, including TFE, vinylidene fluoride, perfluoromethylvinyl ether and chlorotrifluoroethylene to form melt-fabricable, (iodo)cross-linkable polymers.

U.S. Pat. No. 4,243,770 discloses cross-linkable fluorinated polymers containing 0.001 to 10 weight percent of chemically-bound iodine, prepared by polymerizing vinylidene fluoride and, optionally, other fluoromonomers in the presence of a fluorinated iodo compound.

U.S. Pat. No. 4,251,399 discloses cross-linkable polymer blends comprising an iodine-containing fluoroelastomer prepared as in U.S. Pat. No. 4,243,770.

Japanese Application No. J56/72,002 discloses preparation of fluorinated polymers containing pendant groups of the formula, —$O[CF(CF_3)CF_2O]_p(CF_2)_qI$, where p is 0 to 5 and q is 1 to 10, by reacting a fluorinated polymer containing pendant groups of the formula —$O[CF(CF_3)CF_2O]_p(CF_2)CO_2H$ with $I_2$ or I-containing compound in the presence of peroxide.

Japanese Patent Application Nos. J56-95924, J56-95925 and J56-95926 disclose the preparation of cross-linkable fluorinated cation exchange membranes by treating membranes containing pendant —$O(CF_2)_nA$ groups to convert at least some of said groups to iodofunctional groups —$O(CF_2)_nI$; A includes —COF, —$CO_2R$ and —$CO_2M$ where R is $C_1$ to $10$ alkyl and M is an alkali metal or ammonium.

Japanese Patent Appplication No. J53-125986 discloses the conversion, in fluorinated polymeric membranes, of pendant —$OCF_2CF_2I$ groups to —$OCF_2CO_2M$ groups having ion exchange properties (M is metal or ammonium) by means of heat, uv irradiation and/or treatment with chemical reagents such as peroxides, strong sulfur or nitric acids, or amines.

Japanese Patent Application No. J53-131292 discloses the conversion, in fluorinated polymeric membranes, of pendant —$CF_2I$ groups to —$CO_2M$ groups having ion-exchange properties by treatment with an organometallic halide such as magnesium methyl bromide, followed by a reagent such as $CO_2$, $COF_2$, $PX_3$ or $POX_3$ where X is halogen.

SUMMARY OF THE INVENTION

This invention concerns alkyl perfluoro-ω-(2-iodoethoxy) compounds having the formula

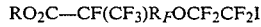
$$RO_2C—CF(CF_3)R_FOCF_2CF_2I \qquad I$$

wherein
$R_F$ is —$OCF_2CF(CF_3)[OCF(CF_3)CF_2]_m$ or $+OCF(CF_3)CF_2+_n$;
m is 0 or an integer of 1 to 7;
n is an integer of 1 to 4; and
R is H, $C_1$ to $6$ alkyl or M where M is an alkali metal.

This invention also concerns vinyl ether monomers of the formula

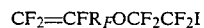
$$CF_2=CFR_FOCF_2CF_2I \qquad II$$

wherein $R_F$ and n are as defined above, and m is an integer of 1 to 7.

This invention also concerns a method for making the iodo-containing compounds, I, comprising reacting a compound of the formula:

$$R^1O_2C-CF(CF_3)R^1{}_F \qquad \text{III}$$

wherein:

$R^1$ is $C_1$ to 6 alkyl;

$R^1{}_F$ is selected from the group consisting essentially of $-OCF_2C(O)CF_3$, $-OCF_2CF(CF_3)[OCF(CF_3)CF_2-]_pOCF(CF_3)COF$, and $[OCF(CF_3)CF_2]_{n-1}OCF(CF_3)COF$;

p is 0 or an integer of 1 to 6, and n is as defined above, with a source of iodine such as ICl or $I_2$, tetrafluoroethylene, and an alkali metal fluoride, in the presence of an aprotic solvent. Preferably, $R^1$ is $-CH_3$ or $-C_2H_5$, the iodine source is ICl, the alkali metal fluoride is KF or CsF, n is 1 or 2, and p is 0 or 1.

DETAILS OF THE INVENTION

In the method for making iodo-compounds I, carbonyl compound III is mixed with an alkali metal fluoride, iodine monochloride (ICl) and TFE in a suitable aprotic solvent, and reacted at a temperature of about 20° to 60° C. for about 30 minutes to 2 days. Reactant molar ratios can be approximately equivalent, although an excess of TFE, ICl and metal fluoride will insure maximum utilization of the more expensive fluorinated carbonyl compound III.

Preferably, compound III is added to a suspension of flame-dried alkali metal fluoride in an aprotic solvent, and stirred until a significant amount of the fluoride is dissolved. ICl is then added, with cooling to maintain a temperature of about 25° C. or below, and the resulting mixture is charged into a dry (moisture-free), tubular metal reactor which is then shaken while TFE is added under pressure. Reaction of TFE with the contents of the tube is accompanied by decreasing pressure, cessation of which indicates that reaction is complete. More preferably, solvent, metal fluoride, ICl and compound III are pre-mixed in the reactor at about 0° to 25° C., followed by addition of TFE, and heating if necessary. Pressure is not critical, but elevated pressures of about 25 to 500 psi (172 to 3,448 kPa) are preferred.

Iodo-compounds, I, can be isolated from the reaction mixture by fractional distillation. It is often convenient to first contact the reaction mixture with cold water and then distill the water-insoluble product.

Suitable aprotic solvents include diglyme, tetraglyme (di- and tetraethyleneglycol dimethyl ether, respectively), tetrahydrofuran, acetonitrile, dimethylformamide, and the like.

Vinyl ethers, II, are prepared by pyrolyzing the iodo-esters over a heated bed of a carbonate, phosphate, sulfite or sulfate salt of an alkali metal or alkaline earth metal, preferably, trisodium phosphate or sodium carbonate; or by direct pyrolysis of an alkali metal salt I in the absence of other salts. The iodo-carboxylic acid salt can be prepared by alkaline hydrolysis of the corresponding iodo-ester. The iodo-carboxylic acid I can be prepared by acid hydrolysis of the corresponding iodo-ester. The iodo-carboxylic acid I can then be converted to the salt by treatment with base.

The fluorinated carbonyl compounds III, wherein $R^1{}_F$ is $-OCF_2C(O)CF_3$, are prepared by reacting fluorinated 1,4-dioxane derivatives with an alkanol or mineral acid to form an acyclic hemiketal ester which is then converted to the ketoester in the presence of $P_2O_5$, as described in U.S. Pat. No. 4,335,255.

The fluorinated ω-fluoroformyl compounds III, wherein $R^1{}_F$ is $-OCF_2CF(CF_3)[OCF(CF_3)CF_2-]_pOCF(CF_3)COF$, are prepared by reacting the ketoester with hexafluoropropene oxide (HFPO), as described in U.S. Pat. No. 4,335,255.

The fluorinated ω-fluoroformyl compounds III, wherein $R^1{}_F$ is $[OCF(CF_3)CF_2]_{n-1}OCF(CF_3)COF$ are prepared by reacting the methyl or ethyl ester of trifluoropyruvic acid with HFPO, as described in U.S. Pat. No. 4,357,282.

Vinyl ethers II can be copolymerized with one or more halogenated 1-olefins. Preferred comonomers are those of the general formula, $CF_2=CR'R''$, wherein R' is H, F, Cl, perfluoroalkyl, or perfluoroalkoxy where the perfluoroalkyl or perfluoroalkoxy radicals contain 1 to 4 carbon atoms, and R'' is H or F. When a perfluoroalkyl- or perfluoroalkoxy-containing olefin is used, at least one other olefin wherein R' is H, F, or Cl should also be present. The copolymers are moldable or otherwise melt-processible and can be thermally cured to fluoroelastomers or to rigid articles.

Films or membranes of said copolymers can be thermally or chemically treated as summarized supra in the "Background" relative to Japanese Application Nos. J53-125986 and J53-131292. Such treatment will convert pendant iodoethoxy groups to carboxylatomethoxy groups $-OCF_2CF_2I \rightarrow -OCF_2CO_2M$ where M is defined as above. Films or membranes can also be treated as described in U.S. Pat. No. 4,164,463 to convert iodo-containing fluoroalkylene groups to phosphonate ester groups, $-CF_2I \rightarrow -CF_2P(O)(OR)_2$, where R is $C_1$ to 12 alkyl or $C_3$ to 12 cycloalkyl. Copolymers containing the carboxylatomethoxy groups or the phosphonate ester groups possess ion-exchange properties and films thereof are useful as membranes in chlor-alkali electrolysis cells.

In the following Examples, which illustrate the invention, all parts and percentages are by weight and temperatures are in degrees Celsius.

EXAMPLE 1

Methyl Perfluoro(8-iodo-2,5-dimethyl-3,6-dioxaoctanoate)

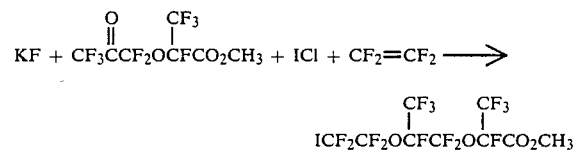

$$\text{ICF}_2\text{CF}_2\text{OCFCF}_2\text{OCFCO}_2\text{CH}_3$$
$$\overset{|}{CF_3} \quad \overset{|}{CF_3}$$

Methyl perfluoro(5-keto-2-methyl-3-oxahexanoate) (54.4 g, 0.17 mol) was added to a suspension of 17.5 g (0.30 mol) of flame-dried KF in 160 ml of tetraglyme stirred at 10° to 15°. After the mixture had stirred until much of the KF dissolved, 54.9 g (0.34 mol) of iodine monochloride was added with cooling to maintain 20°. The resulting mixture was charged into a dry 400-ml metal tube and shaken while tetrafluoroethylene (36 g, 0.36 mol) was added under pressure. When no further pressure drop occurred, gases were vented. The reaction mixture was poured into ice water and decolorized by the addition of $NaHSO_3$. The aqueous layer was extracted with $CF_2ClCFCl_2$, and the combined organic layers were dried over $P_2O_5$ and distilled to give 60.0 g (63%) of methyl perfluoro(8-iodo-2,5-dimethyl-3,6-dioxaoctanoate), bp 81° to 83° (16 mm), pure by GC. IR (neat): 2965 (sat'd CH), 1790 (C=O), 1250–1100 cm$^{-1}$ (CF,C—O). NMR (CCl$_4$): $^1$H 4.03 ppm (s, OCH$_3$); $^{19}$F −64.7 (t,$J_{FF}$ 5.8 Hz, 2F, $CF_2I$), −80.5 (m, 3F, $CF_3$), −83.0 (d, $J_{FF}$ 2.5 Hz, 3F, $CF_3$), −83.7 (m, 2F, $CF_2O$), −132.2 (t of d of m, $J_{FF}$ 16.6, 2.5 Hz, 1F, CF), and −145.9 ppm (t of m, $J_{FF}$ 22 Hz 1F, CF), with AB branches for $CF_2O$ at −7375 and −7518 Hz (M,1F) and −8020 and −8162 Hz (d of m, $J_{FF}$ 22 Hz, 1F).

Anal. Calcd. for $C_9H_3F_{14}IO_4$: C, 19.03; H, 0.53; I, 22.36.

Found: C, 19.18; H, 0.53; I. 22.31.

Subsequent reactions in which unpurified product (obtained after treating with excess cold water) was diluted with $CF_2ClCFCl_2$, washed with water and dried over $P_2O_5$, gave 65 to 85 percent yields of product. A synthesis conducted in acetonitrile as solvent gave the iodoester in lower yield.

EXAMPLE 2

Methyl Perfluoro(8-iodo-2,4-dimethyl-3,6-dioxaoctanoate)

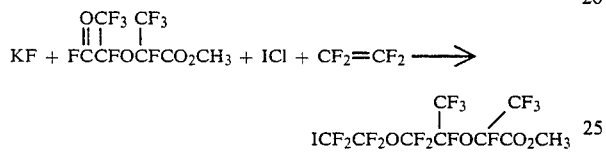

A suspension of 20.9 g (0.36 mol) of flame-dried KF in 130 ml of tetraglyme was treated with 58.0 g (0.18 mol) of methyl 4-fluoroformyl-2-trifluoromethyldifluoro-3-oxapentanoate. The mixture was stirred at 20° for 10 min, then cooled at 10° or less while 58.5 g (0.36 mol) of iodine monochloride was added. The resulting mixture was stirred at 10° for 15 min, then rinsed into a 400-ml metal tube with an additional 30 ml of tetraglyme. The tube was pressured with 50 g (0.50 mol) of tetrafluoroethylene and agitated at 35° to 40° until the pressure had not changed for 2 hr. The reaction mixture was shaken with 500 ml of cold water containing sufficient sodium bisulfite to discharge the iodine color, and the lower organic layer was then washed with 300 ml of water. The metal tube used for reaction was rinsed with $CFCl_3$, and the rinsings were used to extract the aqueous solutions. The combined product and rinsings were then washed with 200 ml of water, dried over $P_2O_5$, and distilled to afford 49.0 g (48%) of methyl perfluoro (8-iodo-2,4-dimethyl-3,6-dioxaoctanoate), bp 77° to 78° (9 mm). IR (neat): 2880 (sat'd CH), 1790 (C=O), 1250–1150 cm$^{-1}$ (CF, C—O). The $^{19}$F NMR spectrum was compatible with the expected 2 racemates of the assigned structure.

EXAMPLE 3

Methyl Perfluoro(11-iodo-2,4,7-trimethyl-3,6,9-trioxaundecanoate)

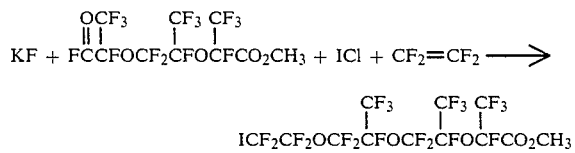

A mixture of 17.4 g (0.30 mol) of flame-dried KF, 160 ml of tetraglyme, and 73.2 g (0.15 mol) of methyl perfluoro- (7-formyl-2,4-dimethyl-3,6-dioxaoctanoate) was stirred for 2 hr at 23°, then stored at 0° overnight. Iodine monochloride (48.7 g, 0.30 mol) was added, the mixture was stirred at 0° for 30 min, and then charged into a 400-ml tube along with 50 g (0.50 mol) of tetrafluoroethylene. Reaction was carried out at 31° for 4 hr, then at 40° for 15 hr. The reaction mixture was washed with a solution of 11 g of $NaHSO_3$ in 300 ml of water, then with 300 ml of water. The aqueous layers were extracted with 50 ml of $CFCl_3$, and the combined product and extracts were washed with water, dried and distilled to afford crude product, bp 69.5° to 72.5° (2.1 mm). Refractionation gave 61.4 g (56%) of methyl perfluoro (11-iodo-2,4,7-trimethyl-3,6,9-trioxaundecanoate, bp 80° to 81° (3.5 mm). IR (neat): 2885 (sat'd CH), 1790 (C=O), and 1250–1150 cm$^{-1}$ (CF,C—O).

Anal. Calcd. for $C_{12}H_3F_{20}IO_5$: C, 19.63; H, 0.41; I, 17.29.

Found: C, 19.80; H, 0.33; I. 17.41.

EXAMPLE 4

Perfluoro(8-iodo-4-methyl-3,6-dioxaoctene-1)

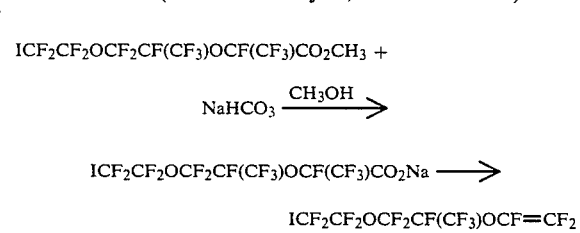

Methyl perfluoro (8-iodo, 2,4-dimethyl-3,6-dioxaoctanoate), 113.6 g (0.20 mol), prepared as described in Example 2 was added to 450 ml of methanol. Sodium bicarbonate (16.8 g, 0.20 mol) was then added and the mixture, protected from light, was stirred at room temperature for 22 hrs, after which time $CO_2$ evolution had ceased. The reaction mixture was then heated to reflux for 3 hr and a clear solution was obtained. Volatiles were removed at 100° to 400° under vacuum (0.1 mm). The salt so prepared was pyrolyzed under vacuum (0.1 mm) at about 140° to 260° C. until $CO_2$ evolution ceased. Approximately 76% of the pyrolysis occurred between 250° and 260° C. Yield of vinyl ether, 70.4 g (71.8%). The product was purified by fractional distillation and its vinyl ether structure was confirmed by gas chromatography and IR analysis.

The embodiments of the invention in which an exclusive property or privilege is claimed are defined as follows:

1. Alkyl perfluoro-ω-(2-iodoethoxy) esters having the formula $$RO_2C-CF(CF_3)R_fOCF_2CF_2I$$

wherein
$R_F$ is $-OCF_2CF(CF_3)(OCF(CF_3)CF_2)_m$ or $(OCF(CF_3)CF_2)_n$;
m is an integer of 2 to 7;
n is an integer and is 1, 3 or 4; and
R is H, $C_{1\ to\ 6}$ alkyl or M where M is an alkali metal.

2. An ester according to claim 1 wherein $R_F$ is $-OCF_2CF(CF_3)(OCF(CF_3)CF_2)_m$.

3. An ester according to claim 1 wherein $R_F$ is $(OCF(CF_3)CF_2)_n$.

4. An ester according to claim 3 wherein R is $CH_3$ or $C_2H_5$ and n is 1.

5. An ester according to claim 4 wherein R is $CH_3$.

6. An ester according to claim 4 wherein R is $C_2H_5$.

* * * * *